United States Patent [19]

Rakestraw

[11] Patent Number: 5,595,876
[45] Date of Patent: Jan. 21, 1997

[54] IN SITU EXTRACTION OF MICROBIAL DNA

[75] Inventor: Scott L. Rakestraw, Newark, Del.

[73] Assignee: E. I. du Pont de Nemours and Company, Wilmington, Del.

[21] Appl. No.: 409,611

[22] Filed: Mar. 22, 1995

Related U.S. Application Data

[63] Continuation of Ser. No. 107,440, Aug. 13, 1993, abandoned.

[51] Int. Cl.$^6$ .................................................. C12Q 1/68
[52] U.S. Cl. .................................................. 435/6; 435/259
[58] Field of Search .............................. 435/6, 259

[56] References Cited

U.S. PATENT DOCUMENTS

| | | | |
|---|---|---|---|
| 4,830,960 | 5/1989 | Appleton | 435/7 |
| 4,830,969 | 5/1989 | Holmes | 435/259 |
| 4,900,677 | 2/1990 | Hewitt | 435/259 |
| 4,935,342 | 6/1990 | Seligson et al. | 435/6 |
| 4,997,932 | 3/1991 | Reardon et al. | 536/27 |
| 5,185,242 | 2/1993 | Keating et al. | 435/6 |

FOREIGN PATENT DOCUMENTS

| | | | |
|---|---|---|---|
| 261956 | 3/1988 | European Pat. Off. | C12P 19/34 |
| 393744 | 10/1990 | European Pat. Off. | C12P 19/34 |
| 0547789 | 6/1993 | European Pat. Off. | C12N 1/06 |
| 0552571 | 7/1993 | European Pat. Off. | C12N 1/06 |
| 1-285858 | 11/1989 | Japan . | |
| WO90/02179 | 3/1990 | WIPO | C12N 15/10 |

OTHER PUBLICATIONS

O. Barsotti et al., *Ann. Inst. Pasteur/Microbio.*, 138:529–536 (1987).
M. Jeanpierre, *Nucliec Acids Research*, 15(22):9611 (1987).
M. Gross–Bellard et al., *Eur. J. Biochem.*, 36:32–28 (1973).
C. D. Reymond, *Nucleic Acids Research*, 15(19):8118–8124 (1987).
J. L. Longmire et al., *Nucleic Acids Research*, 15(2):8590 (1987).
S. A. Miller et al., *Nucleic Acids Research*, 16(3):1215 (1988).
D. D. L. Bowtell, *Anal. Biochem.*, 162:463–465 (1987).
O. Barsotti et al., *Oral. Microbiol. Immunol.*, 3:86–88 (1988).
J. J. Kupiec et al., *Anal. Biochem.*, 164:53–59 (1987).
S. K. Amundesn et al., *Microbios.*, 24:29–39 (1979).
F. Ota et al., *Microbiol. Immunol.* 26(10):957–963 (1982).
T. Ezaki et al., *J. Clin. Microbiol.*, 16(5):844–846 (Nov. 1982).

*Primary Examiner*—Stephanie W. Zitomer
*Assistant Examiner*—Scott W. Houtteman

[57] ABSTRACT

A method for the extraction of microbial DNA which renders such DNA amenable for further enzymatic modification in situ, including digestion of the DNA with restriction endonuclease.

9 Claims, 1 Drawing Sheet

LANE #    1  2  3  4  5  6  7  8  9  10  11  12  13

IN SITU EXTRACTION OF MICROBIAL DNA

This is a continuation of application Ser. No. 08/107,440 filed Aug. 13, 1993, now abandoned.

FIELD OF THE INVENTION

This invention relates to a method for in situ lysis of bacterial cells and subsequent enzymatic modification of the bacterial DNA. The method does not require specific isolation, purification, or separation of the DNA from the bacterial lysate prior to enzymatic modification.

BACKGROUND OF THE INVENTION

Within the rapidly advancing field of microbial diagnostics, research and analytical procedures now require analysis at the nucleic acid level to provide the ultimate identification code unique to each specific microbial strain.

Numerous extraction methods have been developed in attempts to efficiently access these nucleic acids. For diagnostic systems entailing the analysis of a variety of unknown microbes, the method of choice must be capable of simultaneously extracting nucleic acids from a range of bacterial types, including both Gram negative and Gram positive bacteria. Further, a useful method must render extracted nucleic acids which are sufficiently intact and in suitable condition for further biochemical analysis and enzymatic characterization.

U.S. Pat. No. 4,900,677 and European Patent Application 87308431.3 (Hewitt) disclose a procedure for isolating high molecular weight nucleic acids utilizing a mixture of lytic enzymes in combination with a chaotropic agent. Unlike the instant invention, the method necessarily entails a dialysis and concentration step to remove enzyme inhibitors before the extracted nucleic acids may be analyzed enzymatically.

International Patent Application No. PCT/US89/0346 (WO90/102179, Lifecodes Corporation) discloses a broad process for isolating DNA from a range of biological samples, including blood cells, semen, urine, tissue, Hela Cells, hair and *E. coli*. The method states that a separate purification step to remove residual proteolytic activity from lysed cells may be avoided by heating the lysed samples to a temperature and for a time sufficient to autodigest or inactivate residual proteolytic activity. Unlike the instant method, however, this disclosure does not enable a method which has utility in extracting nucleic acids from both Gram negative and Gram positive bacterial strains. Further, in contrast to the instant invention, this disclosure does not demonstrate efficacy in extracting nucleic acids which are suitable for direct enzymatic manipulation in situ.

SUMMARY OF THE INVENTION

This invention provides a process useful for the extraction or purification of nucleic acids from microbial cells. The invention is effective in extracting intact nucleic acids from a broad range of bacteria, including Gram negative and Gram positive strains. The extraction method is performed in situ, and yields nucleic acids which are able to be further enzymatically manipulated in situ.

Specifically, the invention provides an in situ method to extract nucleic acids from microbial cells comprising the steps of (a) heating the microbial cells in the presence of a hypotonic EDTA solution at a temperature and time period sufficient to deactivate endogenous cellular nuclease activity; (b) lysing the microbial cells by addition of achromopeptidase in hypotonic solution and incubating said lysed cells for a time sufficient to inactivate internal cellular degradative factors; and (c) heating said mixture of lysed cells to a temperature sufficient to inactivate remaining protease and nuclease activity; to yield extracted microbial double-stranded nucleic acids which are suitable for further in situ enzymatic manipulation.

In a preferred embodiment, microbial cells are heated to 80° C. for 10 minutes in hypotonic 20 mM EDTA; and then lysed by incubation with added achromopeptidase for 25 minutes at 37° C. The lysed cells are then incubated for 25 minutes at 70° C. to deactivate residual proteolytic or nuclease activity.

In a most preferred embodiment, extracted microbial DNA is then enzymatically treated with a restriction endonuclease within the same cellular extraction vessel, and the restriction digest is electrophoretically chromatographed on a gel whereby the resulting restriction pattern is visualized and compared against known patterns as a means to identify an unknown strain of bacteria.

DETAILED DESCRIPTION OF THE INVENTION

Figure 1:
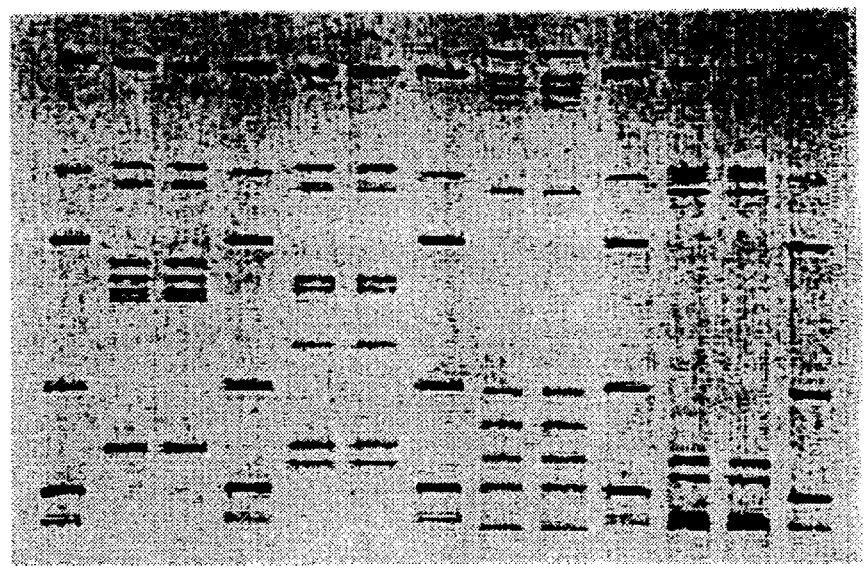
FIG. 1 shows the electrophoretic pattern of an agarose gel of Gram positive and Gram negative bacterial DNA which was extracted using the disclosed method and digested with the restriction endonuclease EcoRI, labeled with a DNA probe; and visualized using chemiluminescent labeling.

Described herein is a method for the in situ isolation and optional further in situ enzymatic manipulation of nucleic acids, preferably DNA, derived from microorganisms, preferably bacteria. This method comprises:

(a) thermally treating the microorganism cells to deactivate the endogenous nuclease activity associated with the cells;

(b) lysing the microorganism cells to release the component DNA and incubating the DNA to render it amenable to subsequent enzymatic action; and (c) deactivation of residual nuclease and protease activity by thermally treating to denature remaining nucleases and proteases.

Optionally, (d) further enzymatic modification of the DNA in the same reaction vessel may be performed.

In the present invention, steps (a)–(d) are made to occur without intermediate isolation, separation, or purification of the DNA and are effective on both Gram positive and Gram negative bacteria. Furthermore, it is an advantage of the present invention that the process can be performed in a single vessel. It is yet another advantage of the present invention that the process can be performed entirely with reagents supplied in the liquid phase. Thus, the method is easily automatable.

For purposes of the present disclosure, Applicant intends that the following terms convey the meanings set forth below.

In situ is used throughout to indicate that the total method described (i.e., the extraction of microbial DNA and optional further enzymatic digestion) can be carried out within a single vessel.

The term "DNA" refers to native, double-stranded deoxyribonucleic acids. For convenience, Applicant throughout the text refers to DNA or nucleic acids interchangeably, but intends to include all classes of nucleic acids, such as RNA and DNA from any source within a microbial cell.

Microbial cells includes all classes of Gram positive and Gram negative bacteria.

Hypotonic refers to any solution possessing an osmolality of dissolved solutes below that which is commonly observed for the interior of intact microbial cells.

By the term "extraction", as used in the phrase "in situ extraction of nucleic acids from cells", Applicant means that the microbial nucleic acids become disassociated from their natural intracellular packaging while remaining intact in a native, double-stranded form. The extraction renders the nucleic acids accessible in solution for further manipulation.

By the term "suitable for further in situ enzymatic manipulation", Applicant refers to the fact that the extracted DNA is now accessible for digestion with enzymes which may be added to the same reaction vessel. Applicant also specifically contemplates and includes within this descriptive phase that such extracted nucleic acids are also rendered accessible and suitable for procedures other than direct enzymatic manipulations, such as labeling or characterization by other means known in this art.

The invention is particularly described and discussed in the following set of steps which are set forth, for purposes of illustration only, using bacterial DNA which is extracted and then further digested with the restriction endonuclease EcoRI.

(a) Deactivation of the Endogenous Nucleases. The first step in the method is heat treatment of the intact bacterial cells, which in combination with the presence of hypotonic EDTA (approximately 20 mM), causes disruption of cell walls, and inactivation of the endogenous nucleases. Failure to initially inactivate the endogenous nucleases frequently results in spontaneous degradation of the bacterial DNA during further processing of the cellular material. Applicant has found particularly that Gram negative cells (in particular Salmonella spp.) were observed to display extensive endogenous nuclease activity in the absence of adequate heat treatment. The optimal time-temperature treatment was found to be $80\pm2°$ C. for 10 minutes in basal lysis buffer (1 mM Tris, 20 mM EDTA, pH 8.0). While heat treatments for less than 10 minutes at 80° C. did yield adequate results for some cell lines (particularly the Gram positive cell lines), such treatments were determined to fail for a significant proportion of cell lines under study. In a similar manner, treatment temperatures less than $80°\pm2°$ C. for 10 minutes did not deactivate the endogenous nucleases for all cell lines studied. Treatment temperatures in excess of 80° C. led to rapid denaturation of the double-stranded DNA contained in the bacterial genome, and inability to produce the subsequent restriction digest. Failure to heat treat the cells at all led to severe DNA degradation for most cell lines studied.

Integral to deactivation of endogenous nucleases is the presence of EDTA. The EDTA chelates the divalent cations which are known to stabilize the organization of the bacterial cell wall. Furthermore, almost all of the endogenous nucleases in the bacterial kingdom are known to be metalloenzymes dependent on divalent cations for their activity. Insufficient EDTA allows the cell wall to remain stable to lytic enzymes, and preserves endogenous nuclease activity. The optimal concentration of EDTA for the range of reagents used generally was found to be 20 mM in the presence of 1 mM Tris at pH 8.0. In this system, below a concentration of 5 mM EDTA, DNA degradation was observed for most cell lines. Above a concentration of 30 mM EDTA, complications with the activity of the enzyme ACP were noted.

(b) Lysis of the Bacterial Cells. The second step of the method is incubation of the cells with the bacteriolytic peptidase achromopeptidase (ACP), which causes rupture of peptide bonds in the cell wall leading to a loss of integrity of the cellular structure. Because this procedure is performed under hypotonic conditions, disruption of the cell wall leads to cell lysis as a result of the high internal osmotic pressure gradients found in bacterial cells.

The peptidolytic enzyme achromopeptidase (ACP) has been known to possess bacteriolytic activity for some time. Previous reports have focused on the lytic activity of the enzyme for Gram positive cells. In the present work, suprisingly, Applicant has determined that the enzyme functions equally well as a general bacteriolytic enzyme under appropriate conditions. The stock concentraction of ACP was varied in the range 250–4000 Units/ml of crude preparation (Wako Chemical, Inc., Richmond, Va.) in deionized water solution. Below a stock concentration of 500 Units/ml the ACP concentration was found to be insufficient to cause general lysis of bacteria in less than 45 minutes (37° C.). At stock ACP concentration of $\geq 500$ Units/ml, bacterial lysis was determined to be complete in 25 minutes for all cell lines studied. However, above stock ACP concentration of 1000 Units/ml the residual proteolytic activity of the ACP required extensive heat treatment in order to inactivate the enzyme prior to introduction of the restriction endonuclease. Preferred mode is to use a stock concentration 500 Units/ml because such concentration provided rapid bacterial lysis (t=25 minutes at 37° C.) without undue difficulty in the abolishment of residual proteolytic activity in the next process step.

A target time of 30 minutes or less was found to be optimal for the lysis step at 37° C. In light of this goal, an ACP concentration of 500 Units/ml was found to be sufficient to cause complete bacterial lysis in 25 minutes at 37° C. Lytic incubation times less than 25 minutes must be avoided as they were found to yield incomplete lysis for some bacterial cell lines studied. Incubation for up to 60 minutes at an ACP concentration of 500 Units/ml and 37° C. was not noted to adversely affect the process.

Product literature for the enzyme (Wako Chemical, Inc., Richmond, Va.) indicates that several cations are known inhibitors of the enzymatic activity. These inhibitors are summarized in the table below. In addition, the present study found that total cation concentrations exceeding 25 mM should be avoided for any cation. For these reasons, crude ACP preparations must always be prepared in deionized water.

Because ACP is a peptidase, it will display non-specific proteolytic activity, including autodigestion. ACP should thus be stored in the dry state at 4° C. or frozen (–20° C.) in deionized water in order to avoid autodigestion of the enzyme. Under either of these conditions, no appreciable loss of enzyme activity for periods up to one year have been observed.

Some proteins were found to interfere with the action of ACP. Prior to the current embodiment, the process used a cocktail of both ACP and lysozyme to affect the lysis of bacterial cells. The cationic nature of lysozyme at physiological pH was found to inhibit the activity of ACP.

| Known Inhibitors of Achromopeptidase Activity | | |
| --- | --- | --- |
| Reagent | Percent Relative ACP Activity at $10^{-3}$M | Percent Relative ACP Activity at $10^{-4}$M |
| None | 100 | 100 |
| $Ca^{++}$ | 51 | 88 |
| $Mg^{++}$ | 54 | 91 |
| $Ba^{++}$ | 51 | 82 |
| $Mn^{++}$ | 33 | 91 |
| $Zn^{++}$ | 0 | 0 |
| $Cd^{++}$ | 5 | 15 |
| $Hg^{++}$ | 0 | 0 |
| $Fe^{++}$ | 5 | 56 |
| $Co^{++}$ | 16 | 41 |
| $Ni^{++}$ | 21 | 56 |
| $Pb^{++}$ | 16 | 62 |
| $Cu^{++}$ | 0 | 10 |
| $Ag^{++}$ | 34 | 48 |
| $Al^{+++}$ | 0 | 56 |
| EDTA | 100 | — |
| 2-Mercaptoethanol | 95 | — |
| Sodium Azide | 100 | — |
| SDS | 53 | — |

Data from Wako Chemical, Inc. (Richmond, VA)

Treatment of DNA to Render it Amenable to Subsequent Manipulation. Once the DNA has been released from the lysed cells, it must be treated to remove bound proteins and other cellular debris before it can be digested with a restriction endonuclease. Due to its native peptidolytic activity, ACP is thus employed as a double agent to both lyse the cells as well as degrade proteinaceous substances that may interfere with subsequent processing. No further reagent additions are needed to allow ACP to perform its proteolytic task. This process step occurs simultaneously with the bacterial lysis. Incubation of the cell lysate at 37° C. promotes the action of ACP.

(c) Deactivation of Residual Nuclease and Protease Activity. Before the bacterial DNA can be enzymatically digested with for example, a restriction endonuclease, residual endogenous nuclease and protease activity must be abolished. Treatment of the cell lysate at high temperature (70°±1° C.) is used to accomplish the goal. Such treatment leads to thermal denaturation of the remaining nucleases and proteases. Particularly, the beneficial ACP proteolytic activity employed to strip the DNA of bound proteins during lysis must be removed before the restriction digest can proceed. Because external digestive enzymes such as EcoRI will subsequently be introduced in very small amounts, any residual proteolytic activity would rapidly destroy external enzymatic activity and result in undigested or partially digested DNA. Remaining protease activity was found to be abolished by the action of heat to thermally denature the proteases. Temperature is of the utmost importance in this operation. The optimal temperature was determined to be 70°±1° C. Temperatures above 71° C. were observed to melt the double-stranded genomic DNA, resulting in incomplete restriction digests and spurious smeared DNA bands as observed by agarose gel electrophoresis. Temperatures below 69° C. resulted in inefficient destruction of the protease activity. Below 65° C. protease activity could not be destroyed in less than 60 minutes of incubation time. Because a target of ≈30 minutes was set for the protease deactivation time, an optimal condition of 70°±1° C. for 30 minutes was determined.

(d) Optionally, the extracted DNA may now be further enzymatically digested in situ. One example is the digestion of the lysate with the restriction endonuclease EcoRI to generate a spectrum of DNA fragments. In this embodiment, excess magnesium ions must be added to overcome the chelation inhibition of the EDTA used in step (a). In addition to the requirement for appropriate buffer conditions, RNAse A is added to the reaction mixture during this step in order to degrade bacterial RNA. Failure to degrade the bacterial RNA can cause spurious signal to be observed after electrophoretic processing, and in extreme cases, can cause inhibition of the activity of the restriction endonuclease.

In one most preferred embodiment of the method, the resulting restriction digest is further analyzed by gel electrophoresis and DNA probe methods to generate a band pattern which may be used to identify or characterize the bacteria [U.S. Pat. No. 4,717,653 (Webster); U.S. Pat. No. 5,087,558 (Webster); U.S. Pat. No. 4,885,697 (Hubner)]. The restriction digest is first terminated by the addition of the loading buffer. The loading buffer contains EDTA, which stops the digestion reaction. Moreover, the loading buffer contains a densifying agent (e.g., Ficoll, sucrose) in order to prepare the digested DNA for loading onto an agarose separation gel. The agarose gel electrophoresis may then proceed by routine methods well known in the art, to yield an electrophoretic pattern of bacterial DNA fragments.

ALTERNATIVE UTILIZATION OF THE EXTRACTED DNA

While the above-described process for Applicant's method includes a restriction endonuclease digestion of DNA as the last step, Applicant believes the disclosed process is also suitable for performing a variety of other manipulations of the harvested DNA. Each modification (with the exception of PCR) described below may be inserted in the claimed method after the high temperature deactivation of step (c). Examples of such enzymatic manipulations and procedures include:

Performance of DNA amplification reactions. A variety of nucleic acid amplification procedures could be employed after step (c) in the above procedure including, for example: polymerase chain reaction (PCR, U.S. Pat. No. 4,683,195); ligase chain reaction (LCR, EPO Publication No. 0 473 155 A2); or random amplified polymorphic DNA analysis (RAPD, U.S. Pat. No. 5,126,239). Addition of the desired polymerases (or ligases, etc.), appropriate primers, deoxynucleotides, and a suitable reaction buffer to the DNA generated will allow DNA amplifications to proceed in the usual manner. Because some amplification reactions require high temperatures (≧75° C.) as an integral part of the process, it may be possible to obviate the need for a separate high temperature step (c) in the basic method.

Other enzymatic operations performed on the DNA. A variety of other DNA manipulation enzymes are routinely used in molecular biological work. For example, one might employ ligases, DNA polymerases, phosphatases, endo- or exo- nucleases, non-specific DNAses, or other enzymes which can label or modify DNA. Furthermore, transcription enzymes (e.g., T7 or SP6 RNA polymerase) may be used to transcribe the DNA template into corresponding RNA copies in the presence of the appropriate nucleotides and buffers.

Labeling of DNA substrates for the purpose of generating DNA probes. A common objective of molecular biological work is the production of DNA probes which are labeled for use as a nucleic acid detection agent. For example, nick translation protocols are routinely used to label the DNA substrates via enzymatic action. In addition, labels containing chemically reactive linking groups (e.g., Photobiotin, fluorescein derivatives) may be added in situ to the DNA for the purpose of labeling or otherwise modifying the DNA.

Cloning experiments. Some molecular biology experiments or processes seek to produce clonal libraries of recombinant DNA. These libraries are usually generated by (1) fragmenting the substrate DNA with restriction endonucleases or other nucleases; (2) adding the desired exogenous DNA insert fragment to the fragmented substrate DNA; (3) ligating the insert fragment to the substrate fragments with ligases; and (4) screening the recombinant DNA produced via probing of the DNA extracted from clones carrying a particular insert. Most of the steps involved in a cloning experiment use enzymatic manipulations of DNA. Thus, a clonal library may be constructed in situ using the methodology described herein.

| General Reagents | |
|---|---|
| Basal Lysis Buffer | 1 mM Tris, 20 mM $Na_2EDTA$, pH 8.0 |
| Achromopeptidase | 500 Units/ml (WAKO-crude fraction; 0.5 mg/ml) in deionized water |
| Digestion Buffer | 160 Units/ml RNAse A (Sigma; 2 mg/ml), 280 mM Tris, 560 mM NaCl, 89 mM $MgCl_2$, 6 mM dithioerythritol, pH 7.5 |
| EcoRI Enzyme | 50 Units/μl (Boehringer-Mannheim) |
| Loading Buffer | 10% Ficoll (Pharmacia), 2 mM EDTA, traces of bromophenol blue and xylene cyanol added as tracking dyes |

EXAMPLE 1

This Example describes the lysis of a Gram negative bacterial species (e.g., *E. coli*) and subsequent in situ EcoRI digestion of DNA obtained from the cells (see lanes 11, 12 and 13 of FIG. 1). *E. coli* bacterial colonies ($5 \times 10^7$ to $5 \times 10^8$ cells) were first retrieved from an overnight Petri plate and suspended in Basal Lysis Buffer to an optical density of 0.40 (600 nm, pathlength=1.0 cm). An aliquot (30 μl) of the cell suspension was added to a sealable reaction vessel, and heated at 80°±1° C. for 10 minutes in a waterbath. The cell sample was allowed to air cool to 37° C. Achromopeptidase (70 μl) was added with mixing to the contents of the reaction vessel. The reaction vessel was held for 25 minutes at 37°±2° C. in order to permit the lysis of the cells. The temperature of the reaction vessel was then raised to 70°±1° C. over a span of 7 minutes and then held at 70°±1° C. for an additional 25 minutes. The purpose of this high temperature step was to deactivate the residual proteolytic activity of the achromopeptidase. Following the high temperature step, the contents of the reaction vessel were allowed to cool to 37°±2° C. over a span of 6 minutes. At this point, the reaction mixture is referred to as the neutralized lysate.

In a separate vessel, 126 μl of EcoRI solution (in the form supplied by the manufacturer, 50 Units/μl) was thoroughly mixed with 576 μl of the Digestion Buffer. An aliquot of this solution (23 μl) was then pipeted into the neutralized lysate mixture from above with thorough mixing. The restriction digestion of the bacterial DNA contained in the neutralized lysate proceeded for 20 minutes at 37° C. At this point, the bacterial DNA had been digested into a spectrum of characteristic fragments by the restriction endonuclease EcoRI. The digestion reaction was terminated and the DNA fragments were readied for electrophoretic analysis by the addition of 10 μl of Loading Buffer. The samples were then electrophoresed on a gel of 0.8% (w/w) agarose, and electroblotted onto a nylon immobilization membrane. The blotted DNA was then contacted with a conserved sequence ribosomal DNA probe as described in U.S. Pat. Nos. 4,717,653 and 5,087,558 (Webster), which are hereby incorporated by reference in their entirety. The probed DNA bands were then visualized using a chemiluminescent system as disclosed in U.S. Pat. No. 5,306,468 which is hereby incorporated by reference. The gel image was then captured (FIG. 1) using a digital CCD camera by techniques well known in the art.

Alternatively, if the DNA fragments are to be used for purposes other than electrophoretic analysis, the digestion reaction may be terminated by the addition of EDTA alone, or by rapid freezing with subsequent storage at −20° C.

EXAMPLE 2

This Example describes the lysis of Gram positive bacterial species (e. g., *Staphylococcus* spp., and *Listeria* spp.) and subsequent in situ EcoRI digestion of DNA obtained from the cells. The extraction, electrophoresis, probe and visualization procedures were conducted exactly as described in Example 1 except with the incorporation of the desired Gram positive strain as the bacterial sample (see lanes 1–10 of FIG. 1). Thus, the general utility of applicant's process in extracting DNA from both Gram positive and negative bacterial species was demonstrated.

| Legend of FIG. 1, for Example 1 and 2 | |
|---|---|
| Lane # | Sample |
| 1 | Image Marker Standard |
| 2 | *Listeria ivanovii* |
| 3 | *Listeria ivanovii* |
| 4 | Image Marker Standard |
| 5 | *Listeria monocytogenes* |
| 6 | *Listeria monocytogenes* |
| 7 | Image Marker Standard |
| 8 | *Staphylococcus aureus* |
| 9 | *Staphylococcus aureus* |
| 10 | Image Marker Standard |
| 11 | *Escherichia coli* |
| 12 | *Escherichia coli* |
| 13 | Image Marker Standard |

What is claimed is:

1. An in situ method to extract nucleic acids from gram negative or gram positive bacterial cells, comprising the steps of:

(a) heating the cells in the presence of a hypotonic EDTA solution at a temperature of 80°±2° C. for about 10 minutes to deactivate endogenous cellular nuclease activity, EDTA being present at concentrations between about 5 mM and 30 mM;

(b) lysing the cells by addition of achromopeptidase in hypotonic solution and incubating said lysed cells for a time sufficient to inactivate internal cellular degradative factors; and (c) heating said lysed cells at a temperature of 70°±1° C. for about 30 minutes to inactivate remaining protease and nuclease activity; to yield extracted bacterial double-stranded nucleic acids which are suitable for in situ restriction digestion, steps (a), (b), and (c) taking place in a single reaction vessel.

2. The method of claim 1 wherein at step (a) EDTA is present at a concentration of about 20 mM in a hypotonic solution of about 1 mM Tris at about pH 8.0.

3. The method of claim 1 wherein at step (b) said lysis is carried out by addition of about 35 Units of achromopeptidase (from a stock solution of 500 units/ml) in a hypotonic solution and incubating, for a period of about 25 minutes at a temperature of about 37° C.

4. An in situ method to accomplish restriction digestion of nucleic acids from gram negative and gram positive bacterial cells, comprising the steps of;
   (a) heating the cells in the presence of a hypotonic EDTA solution at a temperature of 80°±2° C. for about 10 minutes to deactivate endogenous cellular nuclease activity, EDTA being present at concentrations between about 5 mM and 30 mM;
   (b) lysing the cells by addition of achromopeptidase in hypotonic solution and incubating said lysed cells for a time sufficient to inactivate internal cellular degradative factors;
   (c) heating said lysed cells at a temperature of 70°±1° C. for about 30 minutes to inactivate remaining protease and nuclease activity; and
   (d) performing restriction digestion within the vessel of step c, steps (a), (b), (c), and (d) taking place in a single reaction vessel.

5. The method of claim 4 wherein said restriction digestion is performed using the restriction endonuclease EcoRI.

6. The method of claim 5 further comprising after step (d):
   (e) analyzing the product of said enzymatic modifications.

7. The method of claim 6 wherein said analysis is performed on the basis of size separation.

8. The method of claim 7 wherein said separation is achieved through gel electrophoresis.

9. The method of claim 6 wherein said analysis is performed by visualizing or detecting said enzymatically modified DNA using labels or dyes.

* * * * *